(12) United States Patent
Kugler et al.

(10) Patent No.: US 6,273,909 B1
(45) Date of Patent: Aug. 14, 2001

(54) ENDOVASCULAR GRAFT SYSTEM

(75) Inventors: Chad J. Kugler, Andover; John R. Drontle, Monticello; Peter T. Keith, St. Paul, all of MN (US)

(73) Assignee: TERAMed Inc., Maple Grove, MN (US)

( * ) Notice: Subject to any disclaimer, the term of this patent is extended or adjusted under 35 U.S.C. 154(b) by 0 days.

(21) Appl. No.: 09/166,055

(22) Filed: Oct. 5, 1998

(51) Int. Cl.$^7$ .................................................. A61F 2/06
(52) U.S. Cl. ..................... 623/1.13; 623/1.35; 623/1.3
(58) Field of Search ................................. 623/1.35, 1.36, 623/1.49, 1.44, 1.13, 1.15, 1, 1.31, 1.3, 1.32

(56) References Cited

U.S. PATENT DOCUMENTS

| | | |
|---|---|---|
| 4,503,569 | 3/1985 | Dotter . |
| 4,512,338 | 4/1985 | Balko et al. . |
| 4,562,596 | 1/1986 | Kornberg . |
| 4,617,932 | 10/1986 | Kornberg . |
| 4,655,771 | 4/1987 | Wallsten . |
| 4,665,906 | 5/1987 | Jervis . |
| 4,733,665 | 3/1988 | Palmaz . |
| 4,739,762 | 4/1988 | Palmaz . |
| 4,787,899 | 11/1988 | Lazarus . |
| 4,878,906 | 11/1989 | Lindemann et al. . |
| 4,994,071 | 2/1991 | MacGregor . |
| 5,067,957 | 11/1991 | Jervis . |
| 5,078,726 | 1/1992 | Kreamer . |
| 5,104,399 | 4/1992 | Lazarus . |
| 5,122,154 | 6/1992 | Rhodes . |
| 5,123,917 | 6/1992 | Lee . |
| 5,275,622 | 1/1994 | Lazarus et al. . |
| 5,316,023 | 5/1994 | Palmaz et al. . |
| 5,360,443 | 11/1994 | Barone et al. . |
| 5,383,892 | 1/1995 | Cardon et al. . |
| 5,387,235 | 2/1995 | Chuter . |
| 5,395,390 | 3/1995 | Simon et al. ............................ 623/1 |
| 5,397,345 | 3/1995 | Lazarus . |
| 5,397,355 | 3/1995 | Marin et al. . |
| 5,403,378 | 4/1995 | Strecker . |
| 5,405,378 | 4/1995 | Strecker et al. . |
| 5,443,477 | 8/1995 | Marin et al. . |
| 5,449,373 | 9/1995 | Pinchasik et al. . |
| 5,456,694 | 10/1995 | Marin et al. . |
| 5,456,713 | 10/1995 | Chuter . |

(List continued on next page.)

OTHER PUBLICATIONS

Choo et al., "Malignant Colorectal Obstruction: Treatment with a Flexible Covered Stent", *Radiology*, pp. 415–421 (1998).

Chuter et al., "A Telescopic Stent–graft for Aortoiliac Implantation", *Eur. J. Vasc. Endovasc. Surg.* 13, pp. 79–84 (1997).

PCT International Search Report for corresponding PCT Application PCT/US99/23246.

*Primary Examiner*—Cary E. O'Connor
(74) *Attorney, Agent, or Firm*—Popovich & Wiles, P.A.

(57) ABSTRACT

The invention provides an attachment member for anchoring a graft system at a desired location in a vessel of a patient's vascular system. The attachment member comprises a cranial zone having a first radial strength, a caudal zone having a second radial strength, and an intermediate zone having multiple joining longitudinal struts located between and connecting the cranial and caudal zones. The intermediate zone has a third radial strength which is less than the first and second radial strengths, and the cranial and caudal zones are formed from a self-expanding material capable of expanding from a first delivery configuration to a second deployed configuration. The invention also provides an endovascular graft system, a method for deploying an aortic attachment member, and a method for repairing an aneurysm in an aorta.

15 Claims, 9 Drawing Sheets

U.S. PATENT DOCUMENTS

| | | |
|---|---|---|
| 5,489,295 | 2/1996 | Piplani et al. . |
| 5,507,769 | 4/1996 | Marin et al. . |
| 5,522,880 | 6/1996 | Barone et al. . |
| 5,540,712 | 7/1996 | Kleshinski et al. . |
| 5,540,713 | 7/1996 | Schnepp-Pesch et al. . |
| 5,562,728 | 10/1996 | Lazarus et al. . |
| 5,569,296 | 10/1996 | Marin et al. . |
| 5,578,072 | 11/1996 | Barone et al. . |
| 5,591,196 | 1/1997 | Marin et al. . |
| 5,593,417 | 1/1997 | Rhodes . |
| 5,597,378 | 1/1997 | Jervis . |
| 5,609,625 | 3/1997 | Piplani et al. . |
| 5,609,627 * | 3/1997 | Goicoechea et al. ............ 623/1 |
| 5,628,783 | 5/1997 | Quiachon et al. . |
| 5,639,278 | 6/1997 | Dereume et al. . |
| 5,653,743 | 8/1997 | Martin . |
| 5,653,748 | 8/1997 | Strecker . |
| 5,662,700 | 9/1997 | Lazarus . |
| 5,669,936 | 9/1997 | Lazarus . |
| 5,676,696 | 10/1997 | Marcade . |
| 5,683,449 * | 11/1997 | Marcade ............ 623/1 |
| 5,693,083 | 12/1997 | Baker et al. . |
| 5,693,089 | 12/1997 | Inoue . |
| 5,716,365 | 2/1998 | Goicoechea et al. . |
| 5,723,003 | 3/1998 | Winston et al. . |
| 5,723,004 | 3/1998 | Dereume et al. . |
| 5,769,887 | 6/1998 | Brown et al. . |
| 5,776,161 | 7/1998 | Globerman . |
| 5,776,181 | 7/1998 | Lee et al. . |
| 5,782,909 | 7/1998 | Quiachon et al. . |
| 5,800,515 | 9/1998 | Nadal et al. . |
| 5,810,870 | 9/1998 | Myers et al. . |
| 5,817,126 | 10/1998 | Imran . |
| 5,824,036 * | 10/1998 | Lauterung ............ 623/1 |
| 5,824,037 * | 10/1998 | Fogarty et al. ............ 623/1 |
| 5,824,039 | 10/1998 | Piplani et al. . |
| 5,824,040 | 10/1998 | Cox et al. . |
| 5,824,044 | 10/1998 | Quiachon et al. . |
| 5,843,158 * | 12/1998 | Lenker et al. ............ 623/1 |
| 5,843,160 | 12/1998 | Rhodes . |
| 5,843,167 | 12/1998 | Dwyer et al. . |
| 5,851,228 | 12/1998 | Pinheiro . |
| 5,919,225 * | 7/1999 | Lau et al. ............ 623/1 |
| 5,938,697 * | 8/1999 | Killion et al. ............ 623/1 |
| 6,004,347 * | 12/1999 | McNamara et al. ............ 623/1 |
| 6,013,854 * | 7/2000 | Moriuchi ............ 623/1 |
| 6,102,940 | 8/2000 | Robichon et al. ............ 623/1 |

* cited by examiner

Fig. 7A
Fig. 7B
Fig. 7C
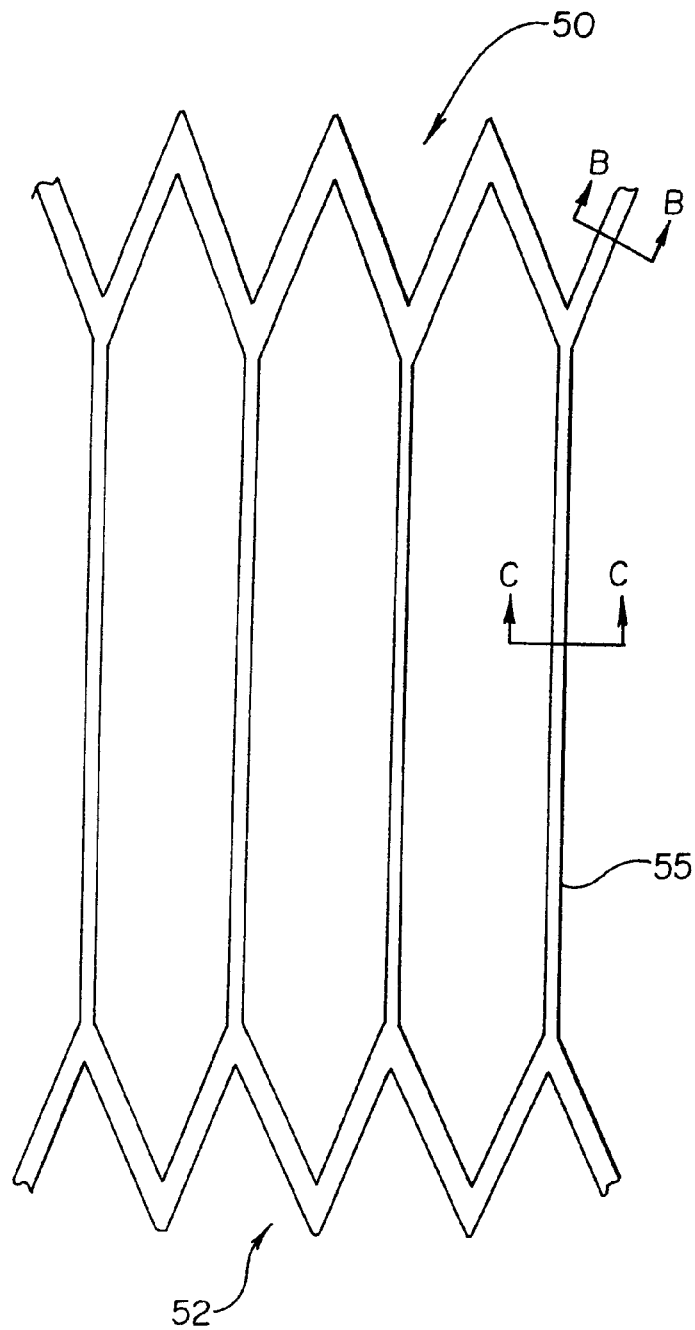

ENDOVASCULAR GRAFT SYSTEM

FIELD OF THE INVENTION

This invention relates to endovascular graft systems for the repair of aneurysms. In particular, this invention relates to an endovascular graft system for use in repairing abdominal aortic aneurysms.

BACKGROUND OF THE INVENTION

Aortic aneurysms represent a significant medical problem for the general population. Aneurysms within the aorta presently affect between two and seven percent of the general population and the rate of incidence appears to be increasing. This form of vascular disease is characterized by a degradation in the arterial wall in which the wall weakens and balloons outward by thinning. If untreated, the aneurysm can rupture resulting in death within a short time.

The traditional treatment for patients with an abdominal aortic aneurysm is surgical repair. This is an extensive operation involving transperitoneal or retroperitoneal dissection of the aorta and replacement of the aneurysm with an artificial artery known as a prosthetic graft. This procedure requires exposure of the aorta through an abdominal incision extending from the lower border from the breast bone down to the pubic bone. The aorta is clamped both above and below the aneurysm so that the aneurysm can be opened and the prosthetic graft of approximately the same size as the aorta is sutured in place. Blood flow is then re-established through the prosthetic graft. The operation requires a general anesthesia with a breathing tube, extensive intensive care unit monitoring in the immediate postoperative period along with blood transfusions and stomach and bladder tubes. All of this imposes stress on the cardiovascular system. This is a high-risk surgical procedure with well-recognized morbidity and mortality.

More recently, significantly less invasive clinical approaches to aneurysm repair known as endovascular grafting have been proposed. (See, Parodi, J. C., et al. "Transfemoral Intraluminal Graft Implantation for Abdominal Aortic Aneurysms," 5 Annals of Vascular Surgery, 491 (1991)). Endovascular grafting involves the transluminal placement of a prosthetic arterial graft in the endoluminal position (within the lumen of the artery). By this method, the graft is attached to the internal surface of an arterial wall by means of attachment devices such as expandable stents, one above the aneurysm and a second below the aneurysm.

Although endovascular grafting represents a desirable improvement over traditional surgical repair, current endovascular graft systems suffer from certain deficiencies. For example, current endovascular graft systems typically are unsuitable for use in an aneurysm which is torturous. Aneurysms in the aorta create tortuosity as they grow. Aneurysms grow both in diameter and length, thus "pushing" the adjacent upper and lower portions of the arteries upward and downward, respectively. Since the aorta is relatively "fixed" at the renal arteries, the portion of the aorta below and near the renal arteries becomes bent and curved in order to accommodate the added length. A similar phenomenon occurs below the aneurysm in the iliac arteries, leading to tortuous iliacs. As many as 20% of aortic aneurysms may have so much tortuosity that they are unable to be fitted with an endovascular graft of this kind. Such systems are unable to conform to the curved walls of the vasculature due to the tortuosity caused by the growing aneurysm.

A specific problem is the "angulation" or bend in the neck of the aorta, where it meets the upper part of the aneurysm. This angulation may result in several problems which limit the effectiveness of traditional endovascular graft systems which do not have designs that conform to the tortuosity and angulation above the aneurysm. First, since these systems are typically anchored above the aneurysm with a stent, a portion of the stent may extend into the blood flow path, creating turbulence which may result in blood clotting. It is well-known that in coronary vessels, stents used to treat constrictive lesions must be well apposed to the wall of the vessel to prevent the possibility of thrombosis. Second, a non-conforming upper stent will not place the upper end of the graft in good apposition to the aortic wall, making it difficult to obtain a good seal with a conventional endovascular graft system. Such is illustrated in FIG. 2, showing a generic endovascular graft attached to a conventional non-conforming expanded metal stent in the neck of a tortuous aortic neck. Since this conventional stent will not conform to the tortuosity of the aorta, an upper edge 1 of the stent extends into the blood flow path increasing the chance of thrombosis. Further, a lower edge 2 is not apposed to the wall of the aorta so that the graft material 3 affixed to it does not properly seal. A third problem with non-conforming attachment systems is that once placed in tortuous or angulated aneurysmal anatomy, they are unstable and can "pop-out" of position. The attachment system shown in FIG. 2 is an example of an unstable attachment system. Conventional endovascular graft systems having an attachment system intended to project across and above the renal artery ostia also pose a different problem since the attachment system obstructs the renal arteries making it difficult, if not impossible, to effect a repair on a renal artery once the stent is in place.

Thus, a need exists for a prosthetic endovascular graft system which will permit stable conformance to bends within an aneurysm, while providing a good seal to the vasculature.

SUMMARY OF THE INVENTION

This invention is an endovascular graft system comprising an attachment member which conforms to the contours of the vessel adjacent an aneurysm, permitting a good seal and robust anchoring of the graft with the vasculature. The attachment member is a stent-like structure which will be referred to herein either as an attachment member, an aortic attachment member or a stent.

In one aspect, this invention is an aortic attachment member capable of expanding from a first delivery configuration to a second deployed configuration for placement in a vessel of a patient's vascular system, the attachment member comprising a cranial zone having a first radial strength, a caudal zone having a second radial strength, and an intermediate zone comprising multiple longitudinal struts located between the cranial and caudal zones, the intermediate zone having a third radial strength. The cranial and caudal zones are separated by and joined by the longitudinal struts. The third radial strength can be lower than the first or second radial strengths. The cross-sectional area of the longitudinal struts is preferably smaller than the cross-sectional area of the material making up the caudal or cranial zones. Preferably, the cross-sectional area is reduced by reducing both the strut width and thickness. Preferably, the caudal and cranial zones have struts patterned in a Z-shape. Alternatively, the cranial zone may have struts shaped in a diamond configuration. The radial strength of the caudal and cranial zones may be approximately equal. In a preferred embodiment, the caudal zone further comprises barbs to assist in anchoring the attachment member. The cranial zone may also comprise barbs to further assist in anchoring the attachment member.

In another aspect, this invention is an endovascular graft system capable of expanding from a first delivery configuration to a second deployed configuration for placement in a vessel of a patient's vascular system. The endovascular graft system comprises an aortic attachment member having a cranial zone and a caudal zone, each having a first radial strength, and an intermediate zone having multiple joining longitudinal struts located between and connecting the cranial and caudal zones, the intermediate zone having a second radial strength which is less than the first radial strength, the cranial and caudal zones being formed from a self-expanding material. The system further includes a conduit formed of a graft material affixed to the caudal zone of the attachment member.

In another aspect, this invention is a biluminal endovascular graft system capable of expanding from a first delivery configuration to a second deployed configuration for placement in a vessel of a patient's vascular system, comprising an aortic attachment member, the aortic attachment member comprising a cranial zone having a first radial strength, a caudal zone having a second radial strength, and an intermediate zone comprising joining longitudinal struts located between the cranial and caudal zones, the intermediate zone having a third radial strength, wherein the cranial and caudal zones are separated by and joined by the longitudinal struts. The system further includes a trunk having first and second branch portions formed of a biocompatible graft material and first and second legs adapted to be deployed in a manner such that they extend from the first and second branches, respectively, the first branch and first leg forming a first conduit and the second branch and second leg forming a second conduit.

In a further aspect, the invention is an attachment member for anchoring a graft system at a desired location in a vessel of a patient's vascular system. The attachment member comprises a first engaging portion, a second engaging portion, the first and second engaging portions comprising a self-expanding material capable of expanding from a delivery configuration to a deployed configuration and an intermediate portion having multiple longitudinal struts, the first ends of the struts being affixed to the first engaging portion and the second end of the struts being affixed to the second engaging portion, the struts being configured such that the first engaging portion can be deployed to engage the walls of the vessel substantially independently of the deployment of the second engaging portion.

In a still further aspect, the invention is an endovascular graft system capable of being deployed at a desired location within a vessel by a catheter introduced into a patient's vascular system. The graft system comprises an attachment member having a first engaging portion, an intermediate portion, and a second engaging portion, the intermediate portion having multiple longitudinal struts having first and second ends, the first ends being affixed to the first engaging portion and the second ends being affixed to the second engaging portion, the first and second engaging portions being formed of a self-expanding material capable of expanding from a delivery configuration to a deployed configuration, the struts being configured such that the first engaging portion may be deployed so that it expands to its deployed configuration while the second engaging portion is in the delivery configuration. The graft system further includes a conduit formed of a graft material affixed to one of the engaging portions of the attachment member.

In a further aspect, the invention is a biluminal endovascular graft system capable of being deployed at a desired location within a vessel by one or more catheters introduced into a patient's vascular system. The graft system comprises an attachment member having a first engaging portion, an intermediate portion and a second engaging portion, the intermediate portion having multiple longitudinal struts having first and second ends, the first ends being affixed to the first engaging portion and the second ends being affixed to the second engaging portion, the first and second engaging portions being formed of a self-expanding material capable of expanding from a delivery configuration to a deployed configuration, the struts being configured such that the first engaging portion may be deployed so that it expands to its deployed configuration while the second engaging portion is in the delivery configuration. The system further comprises a conduit formed of a graft material affixed to one of the engaging portions of the attachment member, a trunk having first and second portions formed of a biocompatible graft material and first and second legs adapted to be deployed in a manner such that they extend from the first and second branches of the trunk. The first branch and first leg forming a first conduit and the second branch and second leg forming a second conduit.

In another aspect, this invention is a method for repairing an aneurysm in an aorta with a graft system having an aortic attachment member as described above attached to a trunk having first and second branches adapted to be mated with first and second legs, thus forming first and second conduits, each conduit comprising a graft component. Each conduit has an iliac attachment element such as a stent at its caudal end to allow the caudal ends of the conduits to be secured within a respective iliac artery. The method comprises advancing the aortic attachment member which is attached to the trunk through an iliac artery by means of a catheter; positioning the aortic attachment member within the neck of the aorta; deploying the first engaging portion of the attachment member so that it seats against the wall of the aorta before the aorta has been substantially occluded by deployment of the second engaging portion; deploying the second engaging portion of the attachment member; advancing the first leg by means of the first catheter through the iliac artery to mate with the first branch of the trunk, thus forming a first conduit; advancing the second leg by means of a second catheter through a second iliac artery to mate with the second branch of the trunk, thus forming a second conduit; and deploying the iliac attachment element of the first and second conduits within the iliac arteries.

In another aspect, the invention is a method for deploying an aortic attachment member in an aorta, the aortic attachment member having first and second engaging portions separated by an intermediate portion, the first and second engaging portions being made of a self-expanding material capable of expanding from a first delivery configuration to a deployed configuration. The method comprises advancing the aortic attachment member and attached trunk through an iliac artery into the aorta by means of a first catheter; positioning the aortic attachment member within the aorta a desired location; deploying the first engaging portion of the attachment member so that it seats against the wall of the aorta before the aorta has been substantially occluded by deployment of the second engaging portion; and deploying the second engaging portion of the attachment member.

BRIEF DESCRIPTION OF THE DRAWINGS

FIG. 7A is a view of a section of the attachment member of FIG. 6A and

FIGS. 7B and 7C are views of cross-sectional views taken along lines B—B and C—C of FIG. 7A, respectively.

DESCRIPTION OF THE PREFERRED EMBODIMENTS

Figure 1:
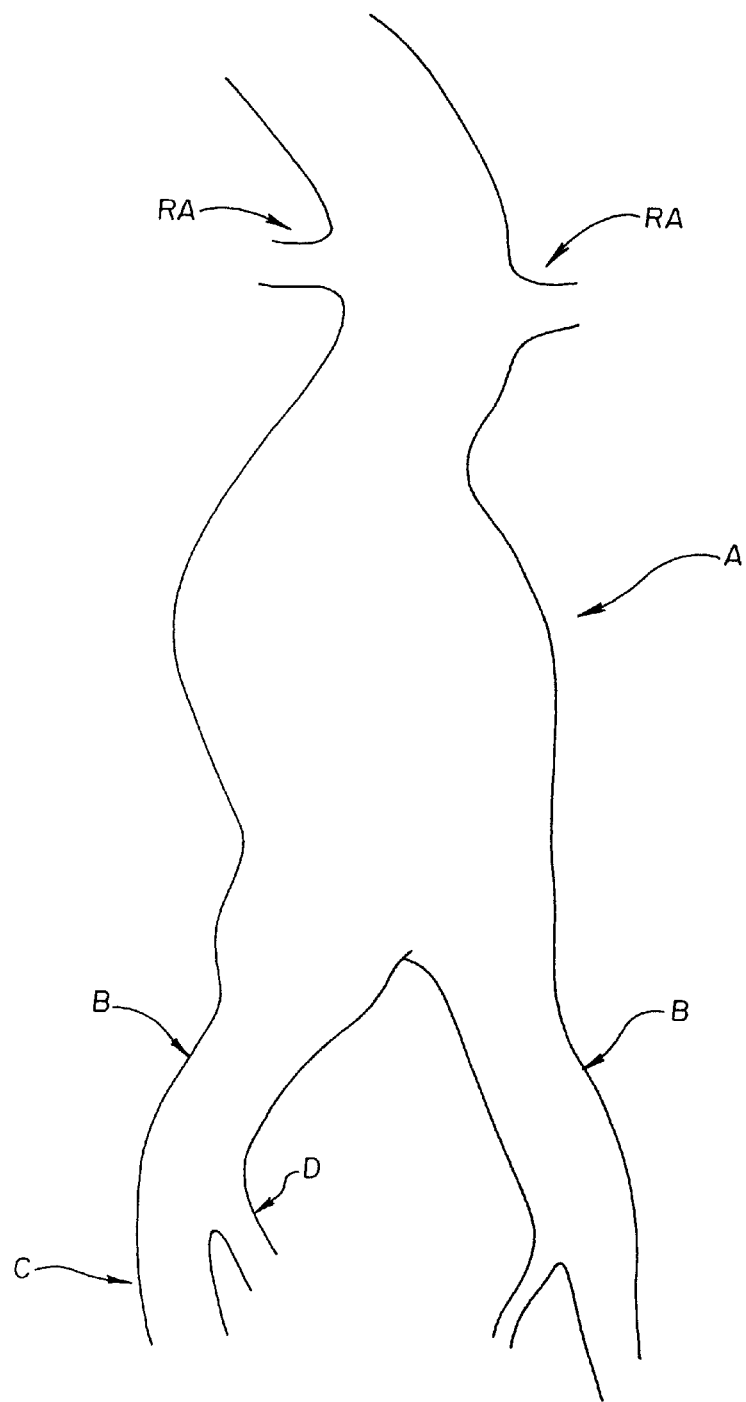
FIG. 1 is a diagrammatic view of a portion of a human vascular system depicting an abdominal aortic aneurysm which extends from below the renal arteries and into the common iliac arteries and which has caused angulation of the aorta above and below the renal arteries.

The terms "distal" and "proximal" as used in this specification refer to the method of delivery of the graft system, not to the vasculature. The preferred method of this graft system contemplates advancement of a catheter in a retrograde manner (i.e., against the flow of blood). Therefore, "proximal" refers to a location closer to the physician and "distal" refers to a location farther from the physician. The vasculature is referred to with respect to the cranial (closer to head) and caudal (closer to feet) directions. Also, as used in this specification, the term "above", in the context of relative positioning with respect to the aneurysm, refers to the region cranial of the aneurysm, for example, within the aorta, whereas "below" refers to the region of the vasculature caudal of the aneurysm, for example, within the common iliac arteries.

The present invention is a graft system and an attachment member for anchoring the graft system within a lumen in a patient's body. Although the specific embodiments disclosed herein relate to an endovascular graft system and attachment member for treating a variety of abdominal aortic aneurysms, particularly those exhibiting tortuosity, it will be understood that the graft system and attachment member have a broader application and are suitable for use in any bodily lumen which may be repaired or reinforced by a graft system. An aortic attachment member attached at the cranial end of the graft material is placed into the aorta above the aneurysm. In some cases, because of the tortuosity of the aorta, or if the non-aneurysmal infrarenal aorta is too short, it may be necessary to place the aortic attachment member across the renal arteries. The diameter of the aortic attachment member is appropriate for a patient's aorta. The aortic attachment member is attached to a graft, typically by sutures. As a result of its unique structural configuration, the aortic attachment member is capable of conforming to the wall of the aorta even in the event of bends or angulations.

The endovascular graft system of this invention may be useful for treating a variety of abdominal aortic aneurysms. For example, a biluminal endovascular graft system may be used for treating aneurysms that extend close to or into the common iliac arteries. In these aneurysms there is not a suitable place within the aorta to seat the lower end of a simple tubular graft. Therefore, the graft must be able to extend into each iliac artery for suitable seating. By "seating" it is meant that the graft is implanted, fixed, or otherwise secured to the vasculature.

The graft of the preferred embodiment is supported internally by individual stents, or stent segments, which are themselves connected to the graft in a manner which secures their position, for example, by sutures. This endovascular graft system is envisioned for use primarily with aneurysms which would benefit from treatment with a biluminal multicomponent endovascular graft system. That is, such a graft system has an attachment member capable of fitting into the neck of an aorta which has been bent or angulated as a result of an aneurysm, a trunk extending from the neck of the aorta into the aneurysm and right and left legs extending from the trunk for connection with a respective common iliac artery. However, depending upon the geometry of the aneurysm, this system could be useful in other graft system designs such as with a unibody bifurcated graft; a tube graft; or a modular two-piece graft having one short segment and one long segment extending from the main body of the graft, and a separate leg which can be joined to the short segment, as is known to one of skill in the art.

Turning now to the Figures, the shape of an aneurysm and the placement and use of the aortic attachment member and endovascular graft system are described.

FIG. 1 depicts an aneurysm A in the infrarenal aorta which extends into the common iliac arteries. Aneurysm A has resulted in causing aorta Ao to become bent or angulated. The infrarenal aorta is that portion of the aorta disposed between the left and right renal arteries RA and the common iliac arteries B which branch left and right. No distinction is made in the figures between elements introduced on the left or the right of the patient's vasculature. Each common iliac artery branches into internal and external iliac arteries, D and C respectively. External iliac artery C becomes the femoral artery below the inguinal ligament. Internal iliac artery D is also known as the hypogastric artery.

Figure 3:
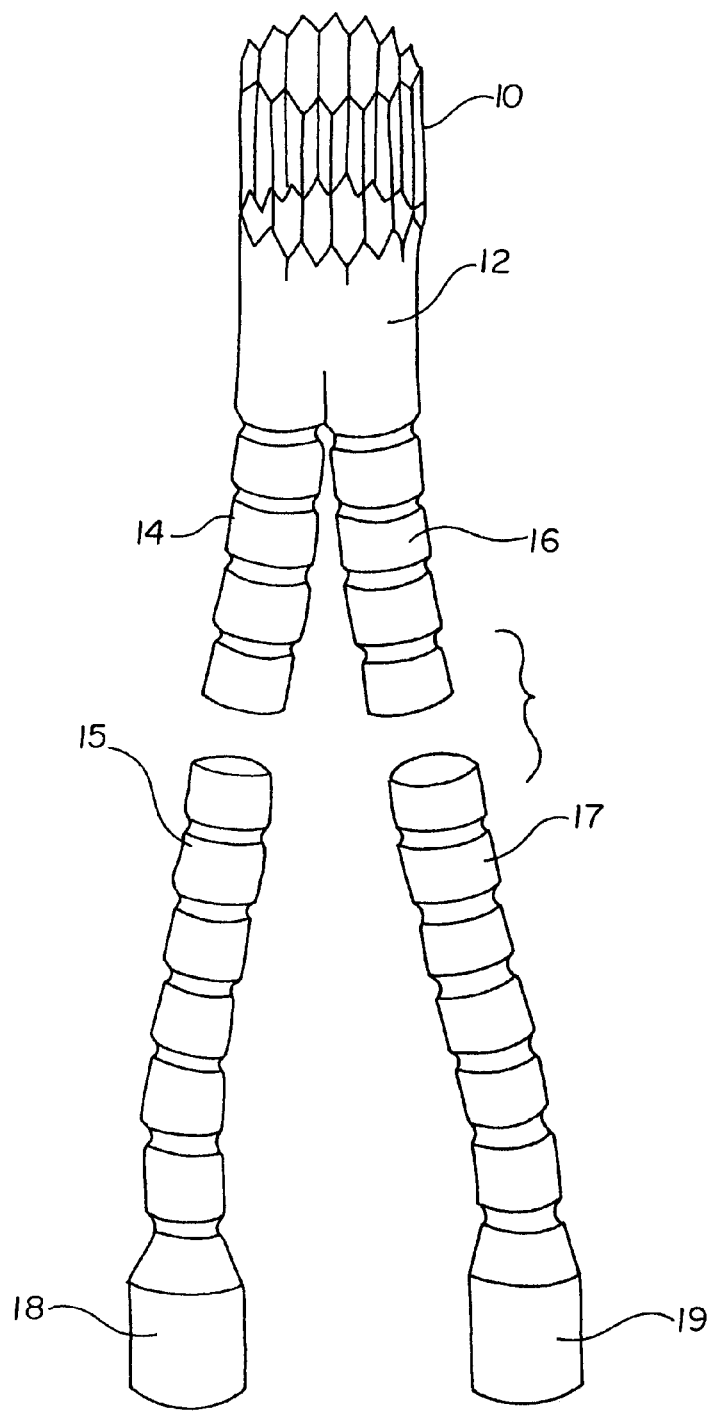
FIG. 3 is a view of a biluminal endovascular graft system of this invention.
Figure 4:
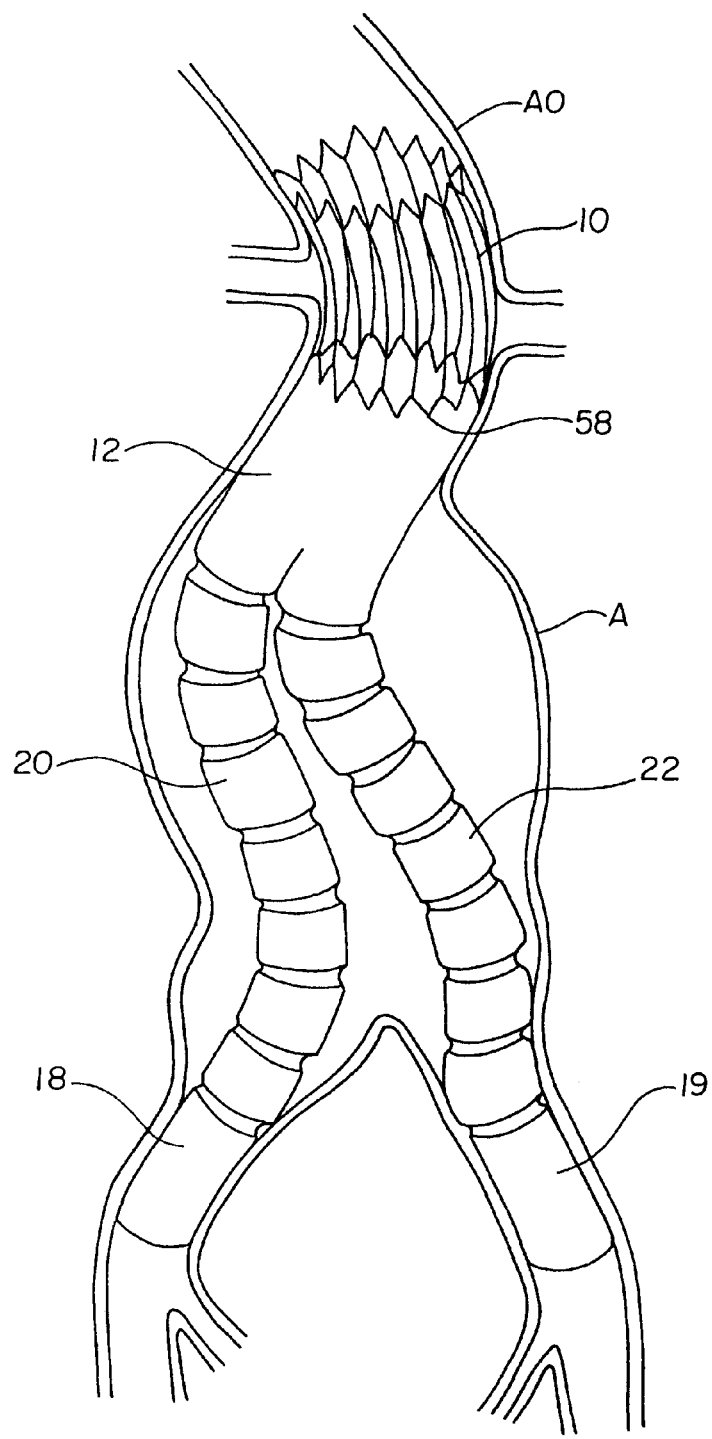
FIG. 4 is a view of the aneurysm of FIG. 1 with the fully deployed biluminal graft system of FIG. 3 in place.

FIG. 3 illustrates a biluminal endovascular graft system and attachment member of the present invention. Aortic attachment member 10 is shown connected to graft material forming trunk 12 which has two branches 14 and 16. Trunk branches 14 and 16 are designed to join with legs 15 and 17, respectively, thus forming a biluminal endovascular graft system. Legs 15 and 17 are designed to be positioned within branches 14 and 16. In a preferred embodiment, the branches overlap the legs at least about 1.5 cm. Once positioned, branch 14 and leg 15 form conduit 20 and branch 16 and leg 17 form conduit 22 as best seen in FIG. 4. The friction of the overlap between the legs and branches keep conduits 20 and 22 from coming apart. At the caudal or proximal end of legs 15 and 17 are positioned iliac attachment elements 18 and 19. Iliac attachment elements 18 and 19 comprise stents which are sutured within an elongated portion of the conduits at the caudal ends thereof and are sized such that when expanded will fix the ends of the conduits within the iliac arteries.

FIG. 4 illustrates the biluminal endovascular graft system fully deployed across an aortic aneurysm. Aortic attachment member 10 is shown conforming to the curvature of the aorta. The endovascular graft system is delivered into the aorta by means of a delivery system such as that described in commonly assigned, co-pending patent application having Serial No. 09/039,776, filed Mar. 16, 1998, entitled "Biluminal Endovascular Graft System", which is hereby incorporated herein by reference. In this system, the femoral artery is entered within the thigh by an arterial incision where the vessel is close to the undersurface of the skin. A guidewire is first endoluminally placed, using conventional techniques to a position in the patient's thoracic aorta, above an aortic aneurysm such as depicted in FIG. 1. The delivery system is guided into the aneurysm along this guidewire. The guidewire remains in a fixed position throughout the endoluminal procedure. Conventional angiography techniques are employed to identify the aneurysm and the position of key anatomical structures such as the renal arteries. The components to be delivered in this manner are compressed relative to their deployed configuration. That is, the material making up the graft system is maneuvered into position and then allowed to expand as described below.

Typically, the graft material of trunk 12 and aortic attachment member 10 are joined together via sutures. Trunk 12 with attachment member 10 and leg 15 are loaded into a single delivery catheter and delivered through one femoral artery into the aorta. Trunk 12 and leg 15 are spaced apart and positioned sequentially in the delivery catheter. Aortic attachment member 10 is moved into the desired position, typically across the renal artery ostia. The catheter is manipulated to withdraw an outer sheath which exposes the aortic attachment member and allows it to expand radially so that it seats within the aorta. Further retraction of the outer sheath allows the entire trunk component 12 with its branches 14 and 16 to fully expand. Right leg 15 of the system is then positioned within the trunk branch 14 and delivered from the same delivery catheter, thus forming conduit 20. Left leg 17 is delivered by means of a separate delivery catheter from the other femoral artery, up the iliac artery and into branch 16 of the trunk. Conduit 22 is thus formed and is identical in structure to conduit 20. The length of the overlap between the branches and legs can be varied by the physician as the system is delivered. Thus, the length of the system can be customized to the patient. At the caudal end of the endovascular graft system the iliac ends of the graft system are positioned within the common iliac arteries to secure and seal the caudal ends of the graft system within the iliac arteries, preferably just above the hypogastric artery ostia.

Figure 5A:
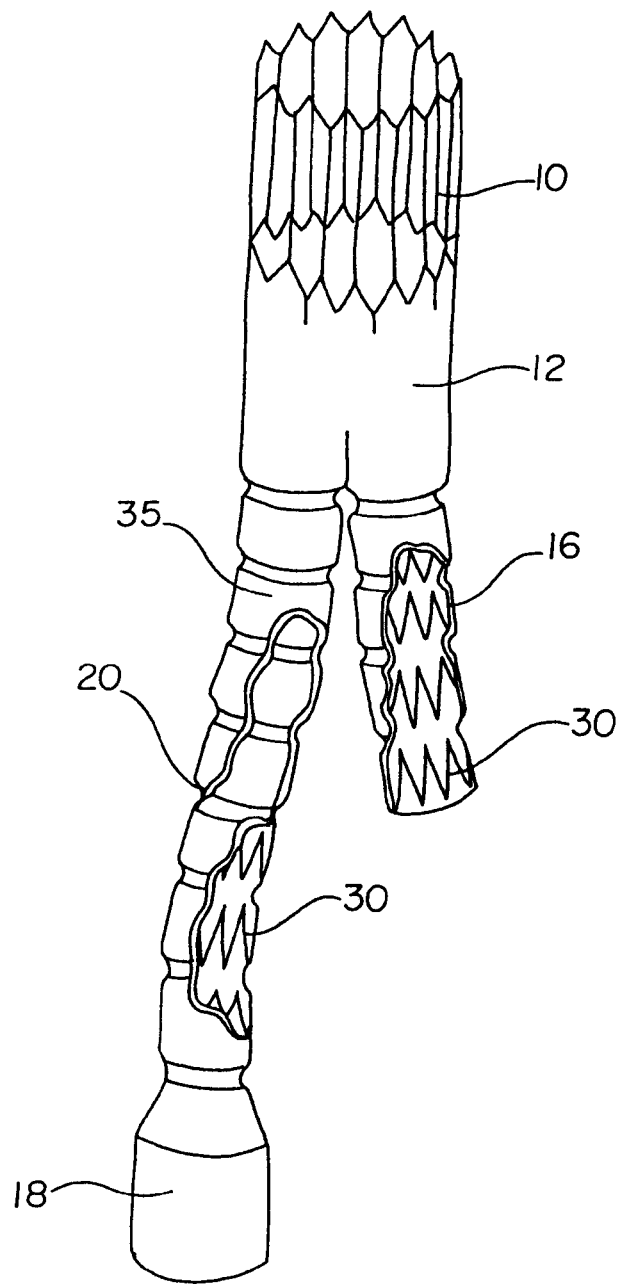
FIG. 5A is a cut-away view of a portion of the biluminal endovascular graft system of FIG. 3 showing stent segments inside the conduits of the endovascular graft system.
Figure 5B:
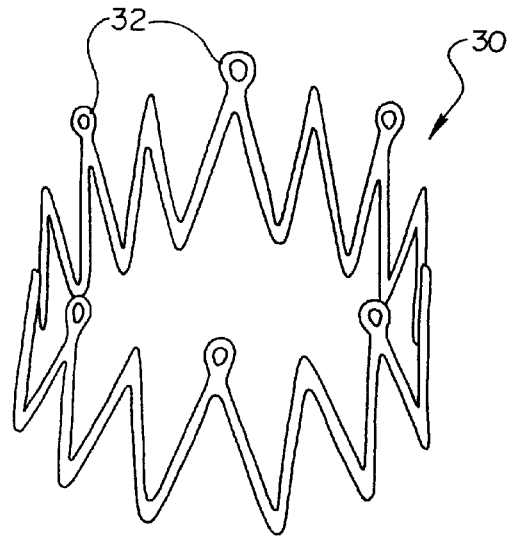
FIG. 5B is a perspective view of an alternative embodiment of one of the stent segments.

FIG. 5A illustrates the endovascular graft system with portions cut away to show the internal structure of conduit 20 and branch 16 descending from trunk 12. The graft system includes stent segments 30 within conduits 20 and 22. FIG. 5B shows an alternative embodiment of a stent segment 30 including an eyelet 32. The stent segments preferably have struts configured in a Z-shape but may have a diamond-shape or other suitable shapes. Suitable shapes are those which would allow for radial expansion and contraction. Typically, these segments are relatively short compared to the total length of a leg. The size and spacing of the stent segments allows for articulation of the legs of the endovascular graft system without the formation of kinks. Thus, the legs are able to bend or elongate to accommodate bends within the aneurysm and iliac arteries. The segments are affixed to graft material 35 by sutures. In the embodiment of FIG. 5B segments 30 are sutured through eyelets 32. Segments 30 are thus held in a desired orientation relative to each other and cannot rotate or slide out of position.

Aortic Attachment Member

Figure 6A:
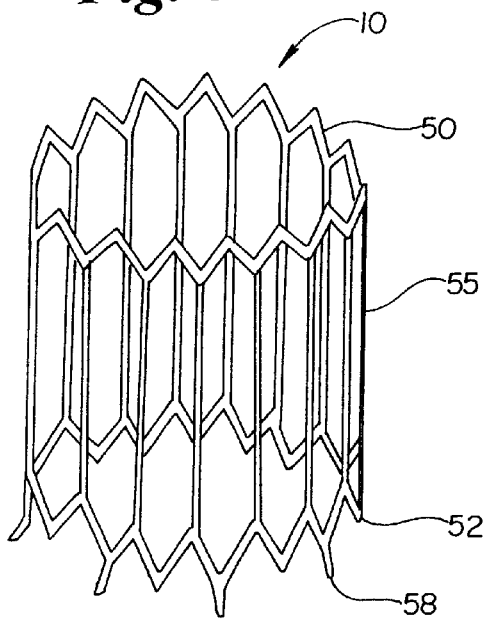
FIG. 6A is a perspective view of the aortic attachment member of the present invention.
Figure 6B:
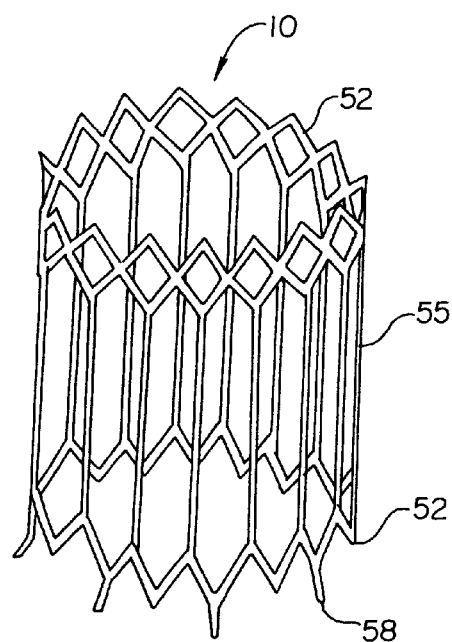
FIG. 6B is a perspective view of an alternative embodiment of the aortic attachment member.

Aortic attachment member 10 is a stent-like structure configured so that there are radially strong cranial and caudal zones 50 and 52 at either end, as depicted in FIGS. 6A and 6B. These zones are configured to permit radial expansion and contraction, as described further below. Typically, these zones have the same configuration and approximately equal radial strength. However, they can have different configurations and thus may have radial strengths that are not the same. The cranial and caudal zones are configured and made of materials that exhibit sufficient radial outward force or radial strength when expanded so that the graft system will be securely anchored within the aorta above the aneurysm when the attachment member is deployed.

Figure 8A:
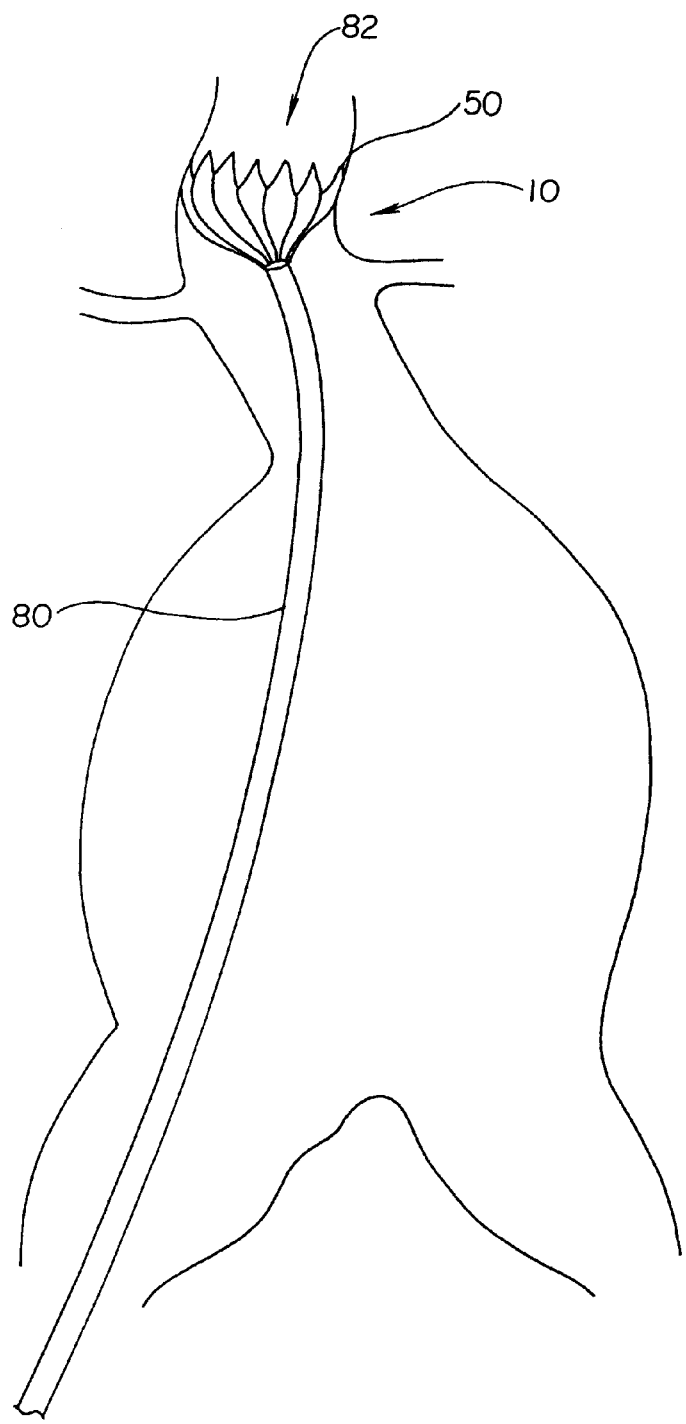
FIGS. 8A and 8B show steps in the deployment of the aortic attachment member of the present invention in an angulated aorta.

The cranial and caudal zones are connected by an intermediate zone comprising multiple longitudinal struts 55. This unique three zone configuration of the attachment member is important for several reasons. First, this configuration allows the cranial zone of the attachment member to be deployed virtually independently of the caudal zone. This is illustrated best by reference to FIGS. 8A and 8B which show deployment of the attachment member in the aorta. For purposes of clarity, the guidewire which would be present during deployment is not shown. In FIG. 8A the sheath of delivery catheter 80 has been partially withdrawn to deploy cranial zone 50 of attachment member 10. Cranial zone 50 can be seen to be securely deployed and seated within the aorta. At this stage of the delivery process blood flowing in the aorta in the direction of arrow 82 is not occluded. Thus, cranial zone 50 has been deployed and seated within the aorta in the absence of force in the direction of arrow 82 which would be exerted had the blood flow been occluded. As a result, cranial zone 50 is deployed precisely where intended.

Figure 8B:
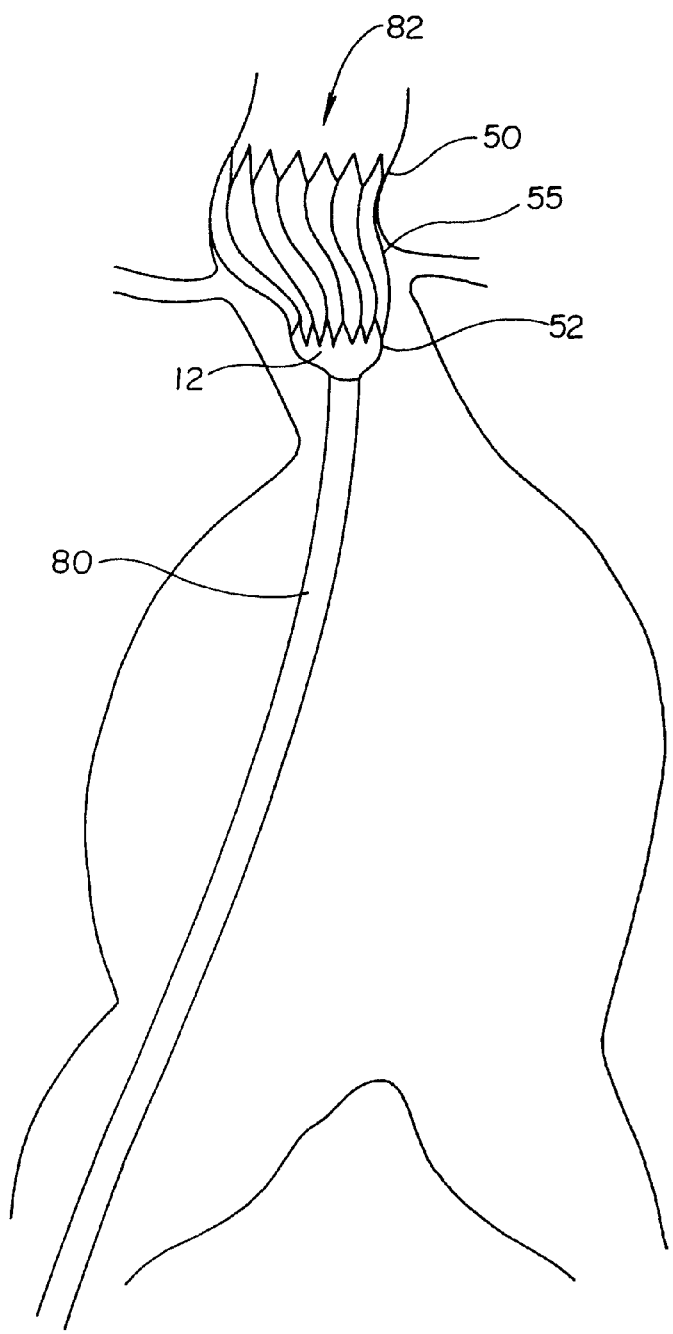

FIG. 8B shows a further stage of deployment after the sheath has been withdrawn past caudal zone 52 partially exposing the graft material of trunk 12. Caudal zone 52 is partially deployed as is trunk 12. It can be seen that the deployment of caudal zone 52 and trunk 12 has partially occluded the aorta. A force in the direction of arrow 82 begins to be asserted against the graft system and increases as caudal zone 52 and trunk 12 expands nearer the wall of the aorta. The position of the attachment member is, however, unaffected by that pressure since the cranial zone 50 of the attachment member has already been fully and securely deployed in the aorta before any significant pressure caused by occluding the aorta has built up.

This constitutes a significant advantage over current graft systems which utilize traditional self-expanding stents to secure the graft system in the aorta above the aneurysm. Stents used in those systems are relatively short, i.e., approximately 2 cm. Since the upper or cranial end of these stents cannot be deployed independently of the lower or caudal end, the result is that the stent is not seated sufficiently upon deployment before the aorta is occluded, creating a large downward force on the partially deployed graft system. Thus, the pressure caused by occlusion of the aorta makes it difficult to properly position such graft systems at a desired location with the aorta.

Figure 2:
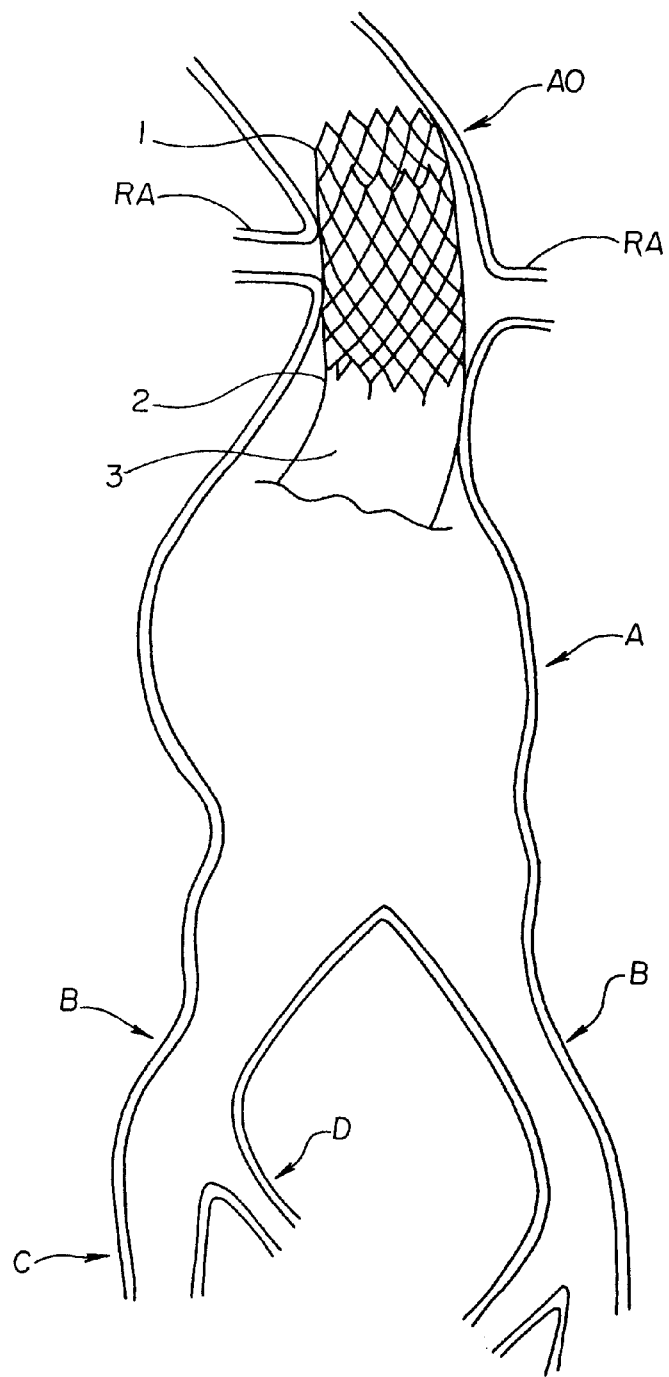
FIG. 2 is a partial view of a conventional Prior Art endovascular graft system deployed in an angulated aorta such as shown in FIG. 1.

Another advantage of the three zoned attachment member is that the longitudinal struts of the transition zone between the cranial and caudal zones allow the attachment member to adapt to angulation or tortuosity of the aorta and still provide a good seal with the wall of the aorta. Just as the quarters at each end of a stack of quarters will remain parallel even if the stack is off-set so will the cranial and caudal zones of the attachment member remain parallel even though the attachment member is deployed in a curved or tortuous aorta as in FIG. 4. In contrast, traditional stents tend not to adapt well to tortuous configurations and do not seal well against the walls of the aorta, as shown in FIG. 2.

A still further advantage of the three zoned attachment member is that it resists longitudinal stretching. Thus, proper positioning upon deployment is easier since the stent will not vary in length during or after delivery by the surgeon.

The longitudinal struts 55 are sufficiently flexible so that they can bend, but they do not elongate axially. The radial strength of the region of the longitudinal struts will be lower than the radial strength of the caudal or cranial zones due to the configuration of the aortic attachment member. Radial strength is the force exerted outward (i.e., from the center of the attachment member) by the cranial and caudal zones and the intermediate zone. That is, these different areas exert radial forces on the vasculature when placed across the aneurysm.

The aortic attachment member is preferably self-expanding and is comprised of a shape memory alloy, such as that described below. The system typically is fabricated by laser cutting a tube of shape memory alloy, then forming the tube to the desired shape.

As illustrated in FIGS. 7B and 7C, the thickness and width of the longitudinal struts is less than that of the material making up the caudal or cranial zones. In this manner, the longitudinal struts are flexible and conformable and do not interfere with the caudal and cranial zones' ability to expand independent of each other. The struts maintain a constant distance between the caudal and cranial zones with the result that these zones remain substantially parallel to one another even when the aortic attachment system is bent. Thus, the aortic attachment system is able to conform to the shape of a tortuous aortic aneurysm yet the attachment system is longitudinally stable. Conventional stent designs which allow bending such as a coil stent or articulation also allow the stents to readily elongate. It is important in this invention that the stent not elongate as the position of the graft must be secure.

In a preferred embodiment, caudal and cranial zones 50 and 52 are each approximately 7 mm in length, and longitudinal struts 55 are approximately 15 mm in length. Approximately 12 mm of the length of the struts 55 are reduced in thickness and width. Caudal and cranial zones 50 and 52 have strut thicknesses and widths between approximately 0.009 inches and 0.014 inches. The reduced regions of longitudinal struts 55 have strut width and thicknesses between approximately 0.007 and 0.011 inches.

Aortic attachment member 10 is sized to fit the aorta. For example, for a 28 mm aorta, the stent diameter should be a minimum of 32 mm. Attachment member is approximately 3 cm in length. It typically is desirable to "oversize" the stent to assure a good seal and engagement within the aorta. A minimum of about 4 mm oversize is preferred. It is also expected that tissue ingrowth occurs faster with an exposed stent (as opposed to a stent covered with graft material), leading to long-term anchoring of the stent. Barbs 58, hooks, or the like may be used to increase the mechanical fixation of the stent to the aorta. If barbs 58 are used, they are preferably placed at the caudal end of the attachment member, as shown in FIGS. 3 to 6. However, they could also be placed at the cranial end. The barbs are preferably sharpened on the end that engages the aorta.

For many aneurysms it is necessary to position the aortic attachment member across the renal arteries in order to properly anchor the system. Although this may be a desirable way to position an aortic attachment member to ensure that it is properly secured within the aorta, such positioning can inhibit blood flow into the renal arteries. The aortic attachment member of this invention crosses the renal artery without significantly inhibiting blood flow. Both the design of the attachment member and the small cross-sectional area of the struts prevent obstruction of blood flow. This minimizes thrombosis and, additionally, provides for subsequent access to the renal arteries.

The aortic attachment member of this invention conforms to a bend or tortuosity in the vessel and does so without any elongation in the stent. That is, it maintains longitudinal integrity unlike a coil or other stents which may bend, but also which can elongate. This is important because the aortic attachment member must stay in the desired position, maintain the seal with the vasculature and prevent the graft from moving axially.

When deployed, the caudal and cranial zones of the aortic attachment member lie against the wall of the vasculature and produce a good seal. The material in these zones may be a diamond shape (FIG. 6B), a Z-shape (FIG. 6A), or other shapes which permit radial expansion and contraction of the system to conform to the size and shape of the aorta and still maintain sufficient radial force to securely anchor the graft system. Moreover, this shape permits different diameters at the caudal and cranial ends of the aortic attachment member. This is an advantage for an aneurysm exhibiting tortuosity. The ability of the attachment member to conform results in good seating of the attachment member in the vasculature so that it cannot move out of position. In addition, the ends of the aortic attachment member do not rest away from the aortic wall as in prior art devices (such as that illustrated in FIG. 2). This can prevent the proper sealing of such graft systems and result in thrombosis. It is also contemplated that the objectives of the present invention can be achieved with an attachment member made up of multiple zones of high radial strength (such as the cranial and caudal zones) connected by multiple zones of longitudinal struts (such as the intermediate zone).

A further advantage of the present invention is that the longitudinal struts separating and joining the caudal and cranial zones can be moved out of the way in the event that further surgery on the renal arteries becomes necessary. This reintervention would be very difficult with the aortic stent of a conventional endovascular graft system in place across the renals. Such systems typically have too many struts to allow them to be moved out of the way for catheters to pass into the renal arteries Even in the case where the present attachment member is comprised of longitudinal struts which are not of reduced thickness or width, they can be easily displaced because of their relatively long length compared to the length of the caudal or cranial zones.

Yet another advantage of the aortic attachment system of this invention is that there is a lower risk of thrombosis. This is because there is less metal and stent structure across the renal arteries than with conventional expanded metal stents.

Stent Structures

Stent segments 30, iliac attachment elements 18 and 19 as well as aortic attachment member 10 preferably are self-expandable and typically are comprised of a shape memory alloy. Such an alloy can be deformed from an original, heat-stable configuration to a second, heat-unstable configuration. The application of a desired temperature causes the alloy to revert to an original heat-stable configuration. A particularly preferred shape memory alloy for this application is binary nickel titanium alloy comprising 55.8% Ni by weight, commercially available under the trade designation NITINOL. This NiTi alloy undergoes a phase transformation at physiological temperatures. A stent made of this material is deformable when chilled. Thus, at low temperatures (e.g., below 20° C.), the stent is compressed so it can be delivered to the desired location. The stent is kept at low temperatures by circulating chilled saline solution. The stent expands when the chilled saline is removed and it is exposed to higher temperatures within the patient's body, e.g., 37° C.

Preferably, the stent is fabricated from a single piece of alloy tubing. The tubing is laser cut, shape-set by placing the tubing on a mandrel, heat-set to its desired expanded shape and size and electropolished. To improve the mechanical integrity of the stent the rough irregular edges left by the laser cutting are removed by a combination of mechanical sandblasting followed by electropolishing. A solution of methanol and sulfuric acid has been shown to work effectively as an electropolishing solution. Preferably, the shape setting is performed at 550° C. for approximately 20 minutes, followed by aging at 470° C. for 70 minutes. This heat treatment process provides for a stent that has a martensite to austenite transformation temperature range of less than 15° C., and an austenite finish temperature ($A_f$) of slightly less than 37° C.

Graft Material

Graft material 35 of trunk 12 and legs 15 and 17 may be made of materials which include woven and knitted materials comprising polyester, polytetrafluoroethylene (PTFE), silicones, and urethanes. The materials may be porous or nonporous and may be opaque to X-rays. Preferred materials include polymers such as polyester fabric, for example DACRON®; polytetrafluoroethylene fabric such as that available as TEFLON®; and other suitable fabric.

A preferred fabric for use in the graft component is a 40 denier polyester yarn, having 180 to 250 end yarns per inch per face and 80 to 120 pick yarns per inch per face. At this weave density, the graft component is relatively impermeable to blood flow through the wall, but yet is relatively thin, ranging between 0.08 and 0.12 mm wall thickness. Preferably, the grafts are woven as tubes with appropriate tapers formed directly on the loom. However, desired dimensions for different regions of the graft component can also be achieved with suture lines or stitching of a flat fabric, or stitching a tubular fabric of an initial uniform perimeter equal to the desired perimeter of the aortic portion. The graft component of each conduit has a generally tubular shape. Prior to attachment of the stents crimps are formed in the graft between the stent positions by placing the graft on a shaped mandrel and thermally forming indentations in the surface.

Although particular embodiments of the invention have been disclosed herein in detail, this has been done for the purposes of illustration only, and is not intended to be limiting with respect to the scope of the appended claims. It is contemplated that various substitutions, alterations, and modifications may be made to the embodiments of the invention described herein without departing from the spirit and scope of the invention as defined by the claims.

What is claimed is:

1. An attachment member for anchoring a graft system at a desired location in a vessel of a patient's vascular system, the attachment member comprising:
   a cranial zone comprising a plurality of interconnected cranial struts, the cranial zone having a first radial strength the cranial struts having a first cross-sectional area;
   a caudal zone comprising a plurality of interconnected caudal struts, the caudal zone having a second radial strength, the caudal struts having a second cross-sectional area; and
   an intermediate zone having multiple joining longitudinal intermediate struts located between and connecting the cranial and caudal zones, the intermediate zone having a third radial strength which is less than the first and second radial strengths, the intermediate struts having a third cross-sectional area which is less than the first and second cross-sectional areas, the cranial and caudal zones being formed from a self-expanding material capable of expanding from a first delivery configuration to a second deployed configuration.

2. The attachment member of claim 1 wherein the material forming the caudal zone forms a Z-shaped pattern.

3. The attachment member of claim 1 wherein the material forming the cranial zone forms a Z-shaped pattern.

4. The attachment member of claim 1 wherein the material forming the cranial zone forms a diamond-shaped pattern.

5. The attachment member of claim 1 wherein the first radial strength is approximately equal to the second radial strength.

6. The attachment member of claim 1 wherein the caudal zone further comprises barbs.

7. The attachment member of claim 1 wherein the intermediate zone has at least three longitudinal struts.

8. The attachment member of claim 1 wherein the cranial struts have a first width and thickness, the caudal struts have a second width and thickness, and the intermediate struts have a third width and thickness, and further wherein the third width and thickness is less than the first and second widths and thicknesses.

9. The attachment member of claim 8 wherein the first width and thickness is approximately equal to the second width and thickness.

10. A stent comprising:
    a first engaging portion comprising first struts having a first cross-sectional area;
    a second engaging portion comprising second struts having a second cross-sectional area, the first and second engaging portions comprising a self-expanding material capable of expanding from a delivery configuration to a deployed configuration;
    an intermediate portion having multiple longitudinal struts having a third cross-sectional area, each of the longitudinal struts having first and second ends, the first ends being affixed to the first engaging portion and the second ends being affixed to the second engaging portion, the intermediate struts being configured such that the first engaging portion can be deployed to engage the walls of the vessel substantially independently of the deployment of the second engaging portion,
    wherein the third cross sectional area is less than the first and second cross sectional areas.

11. The attachment member of claim 10 wherein the longitudinal struts are configured to maintain the first and second engaging portions in a substantially parallel relationship when the attachment member is deployed in a vessel which causes the attachment member to bend.

12. The attachment member of claim 10 wherein the intermediate portion has at least three longitudinal struts.

13. A method for repairing an aneurysm in an aorta with a graft system having an aortic attachment member having first and second engaging portions separated by an intermediate portion, the first and second engaging portions being made of a self-expanding material capable of expanding from a delivery configuration to a deployed configuration, the second engaging portion being attached to a trunk having first and second branches adapted to be mated with first and second legs, thus forming first and second conduits, each conduit comprising a graft component and having an iliac attachment element at its caudal end, the aorta branching into two iliac arteries, the method comprising:

advancing the aortic attachment member and attached trunk though an iliac artery into the aorta by means of a first catheter;

positioning the aortic attachment member within the aorta at a desired location;

deploying the first engaging portion of the attachment member so that it seats against the wall of the aorta before the aorta has been substantially occluded by deployment of the second engaging portion;

deploying the second engaging portion of the attachment member;

advancing the first leg by means of the first catheter through the iliac artery to mate with the first branch of the trunk, thus forming a first conduit;

advancing the second leg by means of a second catheter though a second iliac artery to mate with the second branch of the trunk, thus forming a second conduit; and deploying the iliac attachment element of the first and second conduits within the iliac arteries.

14. A biluminal endovascular graft system capable of being deployed at a desired location within a vessel in a patient's vascular system, comprising:

a first delivery catheter having a retractable outer sheath adapted to be delivered through a first femoral artery;

the first delivery catheter containing therein a first leg and a graft portion comprising an aortic attachment member attached to a trunk having first and second branches, the graft portion and the first leg being positioned in the first delivery catheter in a non-overlapping manner such that the graft portion may be deployed independently of the first leg and the first leg can be deployed thereafter within the first branch of the trunk;

a second delivery catheter having a retractable outer sheath adapted to be delivered through a second femoral artery; the second delivery catheter containing therein a second leg, such that the second leg can be deployed within the second branch of the trunk.

15. A biluminal endovascular graft system capable of being deployed at a desired location within a vessel by one or more catheters introduced into a patient's vascular system, the biluminal endovascular graft system comprising:

an attachment member having a first engaging portion, an intermediate portion and a second engaging portion, a trunk formed of a biocompatible graft material, the trunk being affixed to and extending from one of the engaging portions of the attachment member, such that the other engaging portion and the intermediate portion do not lie within the trunk, the trunk having first and second branches;

first and second legs adapted to be deployed in a manner such that they extend from the first and second branches, respectively, the first branch and first leg forming a first conduit and the second branch and second leg forming a second conduit; and a plurality of spaced apart stent segments lining the first and second conduits and attached to the graft material, the diameter of graft material overlying a stent segment being greater than the diameter of graft material between the spaced apart stent segments.

* * * * *